United States Patent
Nakanishi et al.

[11] 3,935,217
[45] Jan. 27, 1976

[54] SUBSTITUTED PYRROLIDINEMETHANOLS

[75] Inventors: Michio Nakanishi; Hiroshi Yuki, both of Nakatsu, Japan

[73] Assignee: Yoshitomi Pharmaceutical Industries, Ltd., Osaka, Japan

[22] Filed: Feb. 28, 1974

[21] Appl. No.: 446,841

[30] Foreign Application Priority Data
Feb. 28, 1973 Japan................... 48-24528

[52] U.S. Cl................ 260/326.5 R; 260/326.5 D; 260/326.36; 260/326.45; 260/326.47; 424/274

[51] Int. Cl.²...................................... C07D 207/08

[58] Field of Search.............. 260/326.5 R, 326.5 D

[56] References Cited
UNITED STATES PATENTS

| | | | |
|---|---|---|---|
| 3,108,117 | 10/1963 | Wu et al. ........................ | 260/326.5 |
| 3,312,716 | 4/1967 | Biel et al........................ | 260/326.5 |
| 3,732,247 | 5/1973 | Helsley et al. .................. | 260/326.8 |

*Primary Examiner*—Raymond V. Rush
*Attorney, Agent, or Firm*—Sughrue, Rothwell, Mion, Zinn & Macpeak

[57] ABSTRACT

Substituted pyrrolidinemethanols of the formula:

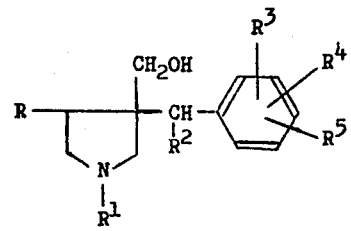

wherein $R^1$ and $R^2$ are each H or $C_{1-4}$ alkyl; $R^3$, $R^4$ and $R^5$ are each H, halogen, $C_{1-4}$ alkyl or $C_{1-4}$ alkoxy, or $R^3$ and $R^4$ combinedly form methylenedioxy; and R is $C_{1-10}$ alkyl or a group of the formula:

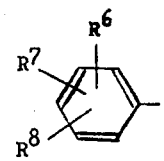

where $R^6$, $R^7$ and $R^8$ are each H, halogen, $C_{1-4}$ alkyl or $C_{1-4}$ alkoxy, or $R^6$ and $R^7$ combinedly form methylenedioxy; and pharmaceutically acceptable acid addition salts thereof are disclosed. They are useful as drugs for the treatment of diseases of the heart and circulation.

21 Claims, No Drawings

SUBSTITUTED PYRROLIDINEMETHANOLS

DETAILED DESCRIPTION OF THE INVENTION

The present invention relates to substituted pyrrolidinemethanols of the formula:

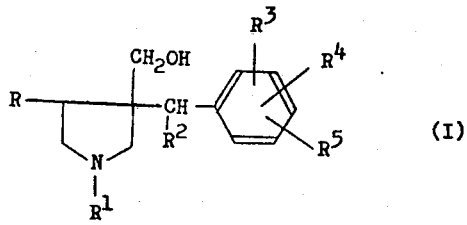

and pharmaceutically acceptable acid addition salts thereof, pharmaceutical compositions containing the said compounds and the use thereof.

In the above formula, $R^1$ and $R^2$ are each a hydrogen atom or an alkyl group of 1 to 4 carbon atoms; $R^3$, $R^4$ and $R^5$ are each a hydrogen atom, a halogen atom, an alkyl group of 1 to 4 carbon atoms or an alkoxy group of 1 to 4 carbon atoms, or $R^3$ and $R^4$ combinedly form a methylenedioxy group; and R is an alkyl group of 1 to 10 carbon atoms or a group of the formula:

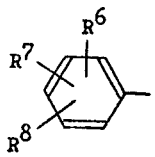

wherein $R^6$, $R^7$ and $R^8$ are each a hydrogen atom, a halogen atom, an alkyl group of 1 to 4 carbon atoms or an alkoxy group of 1 to 4 carbon atoms, or $R^6$ and $R^7$ combinedly form a methylenedioxy group.

The alkyl group represented by R includes methyl, ethyl, propyl, isopropyl, butyl, isobutyl, pentyl, hexyl, heptyl, 1-ethylpentyl, octyl, nonyl and decyl. The halogen atom represented by $R^3$ to $R^8$ includes F, Cl, Br and I. The alkyl group represented by $R^1$ to $R^8$ includes methyl, ethyl, propyl, isopropyl, butyl, isobutyl and tert-butyl. The alkoxy group represented by $R^3$ to $R^8$ includes methoxy, ethoxy, propoxy, isopropoxy and butoxy.

The novel compounds of formula (I) can be produced by subjecting a compound of the formula:

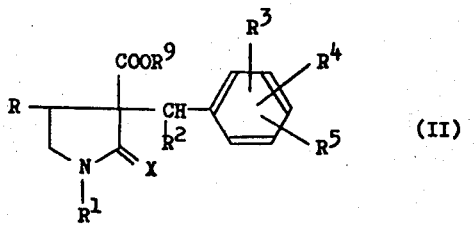

to reduction, wherein R, $R^1$, $R^2$, $R^3$, $R^4$ and $R^5$ are as defined above, $R^9$ is a hydrogen atom or an alkyl group of 1 to 4 carbon atoms, and X is an oxygen atom or a sulfur atom.

The reduction is advantageously carried out with a metal hydride such as lithium aluminium hydride, sodium borohydride, sodium dihydrobis(2-methoxyethoxy)aluminate or diisobutyl aluminium hydride, in an inert solvent such as ethyl ether, butyl ether, tetrahydrofuran, benzene, toluene, xylene, pyridine or triethylamine, at a temperature of from room temperature to a refluxing temperature, for several minutes to ten-odd hours. Other conventional reductions can also be employed according to circumstances, such as reduction with nascent hydrogen (e.g. sodium plus ethanol), catalytic reduction over copper chromium oxide, zinc chromium oxide, Raney nickel or reduced copper, and electrolytic reduction.

The compounds of formula (I) wherein $R^1$ is an alkyl group can also be produced by reacting a compound of formula (I) wherein $R^1$ is a hydrogen atom with an alkylating agent such as alkyl halide, dialkyl sulfate, diazomethane, or formaldehyde and formic acid.

The compounds of formula (I) are obtained in the form of a cis- or trans-isomer, or a mixture thereof. The cis-trans mixture, if desired, can be separated in a conventional manner such as fractional crystallization or column chromatography, and further, each component can be resolved into dextro- and levo-isomers.

The compounds of formula (I) thus produced can be converted into the corresponding acid addition salts in a conventional manner by treating the compound with various inorganic and organic acids, for example, hydrochloric, hydrobromic, sulfuric, phosphoric, formic, acetic, oxalic, maleic, fumaric, tartaric, lactic, malic, mandelic, di-o-toluoyltartaric, benzoic and methanesulfonic acids.

The present invention provides such novel substituted pyrrolidine-methanols of formula (I) as described in the following:

1. 3-(3,4-Dimethoxybenzyl)-4-(3,4-dimethoxyphenyl)-3-pyrrolidinemethanol
2. 3-(3,4-Dimethoxybenzyl)-4-(3,4-methylenedioxyphenyl)-3-pyrrolidinemethanol
3. 3-(3,4,5-Trimethoxybenzyl)-4-(3,4-dimethoxyphenyl)-3-pyrrolidinemethanol
4. 4-Ethyl-3-(3,4-dimethoxybenzyl)-3-pyrrolidinemethanol
5. 4-(3,4-Dimethoxyphenyl)-3-(3,4-methylenedioxybenzyl)-3-pyrrolidinemethanol
6. 4-(4-Chlorophenyl)-3-(3,4-dimethoxybenzyl)-3-pyrrolidinemethanol
7. 3-(3,4-Dimethoxybenzyl)-4-(2-methoxyphenyl)-3-pyrrolidinemethanol
8. 3-(3,4-Dimethoxybenzyl)-4-(4-methoxyphenyl)-3-pyrrolidinemethanol
9. 3-(3,4-Dimethoxybenzyl)-4-phenyl-3-pyrrolidinemethanol
10. 3-(4-Chlorobenzyl)-4-ethyl-3-pyrrolidinemethanol
11. 3-(4-Chlorobenzyl)-4-(4-chlorophenyl)-3-pyrrolidinemethanol
12. 3-(3,4-Dimethoxybenzyl)-4-(3,4-dimethoxyphenyl)-1-methyl-3-pyrrolidinemethanol
13. 3-(2-Methoxybenzyl)-4-(3,4-dimethoxyphenyl)-3-pyrrolidinemethanol
14. 4-(3,4-Dimethoxyphenyl)-3-(4-methylbenzyl)-3-pyrrolidinemethanol
15. 3-(4-Chlorobenzyl)-4-(3,4-dimethoxyphenyl)-3-pyrrolidinemethanol
16. 3-Benzyl-4-(3,4-dimethoxyphenyl)-3-pyrrolidinemethanol
17. 3-Benzyl-4-phenyl-3-pyrrolidinemethanol
18. 3-(3,4-Dimethoxybenzyl)-4-(4-methylphenyl)-3-pyrrolidinemethanol 19. 3-(4-Methoxybenzyl)-4-(3,4-methylenedioxyphenyl)-3-pyrrolidinemethanol
20. 3-(3,4-Dimethoxybenzyl)-4-(3,4,5-trimethoxyphenyl)-3-pyrrolidinemethanol
21. 3-(3,4-Dimethoxy-α-methylbenzyl)-4-(3,4-dimethoxyphenyl)-3-pyrrolidinemethanol
22. 4-(1-Ethylpentyl)-3-(3,4-dimethoxybenzyl)-3-pyrrolidinemethanol
23. 3-(3,4-Dimethoxybenzyl)-4-(3-methoxyphenyl)-3-pyrrolidinemethanol
24. 3-(3-Methoxybenzyl)-4-(3,4-dimethoxyphenyl)-3-pyrrolidinemethanol
25. 4-(2-Chlorophenyl)-3-(3,4-dimethoxybenzyl)-3-pyrrolidinemethanol The compounds of formula (I) and pharmaceutically acceptable acid addition salts thereof exhibit valuable pharmacological actions on the cardiovascular system such as protective action on various experimental arrhythmia, β-adrenergic blocking actions, and protective action on experimental angina pectoris as well as protective action on thrombus. For example, the protective activity against ouabain induced arrhythmia of the compounds of the invention is illustratively demonstrated according to the following method:

The experimental procedure employed was essentially identical to that described by E. M. Vaughan Williams et al. in "The Lancet", vol. 1, pp. 420–421 (1963). Male guinea pigs each weighing 250–350 g were anesthetized with urethane (1.6 g/kg) intraperitoneally. Common carotide artery blood pressure and electrocardiogram (Lead II) were monitored during 30 minutes. Ouabain (10 μg/kg) was infused during 30 seconds in every 2 minutes and electrocardiogram was recorded for 5 seconds in every 2 minutes. Note was made of the dose required to produce cardiac arrest. The dose of ouabain required to produce cardiac arrest after intravenous administration of test compound at a dose of 3 mg/kg was established in the same manner, and compared with that dose found in the control group.

The results are summarized in the following table:

Amount of Quabain (μg/kg)

| Treatment | Cardiac Arrest |
| --- | --- |
| Control | about 160 |
| Test Compound A | > 300 |
| Test Compound B | > 300 |

Test Compound A: 3-(3,4-dimethoxybenzyl)-4-(3,4-dimethoxyphenyl)-3-pyrrolidinemethanol sulfate.
Test Compound B: 3-(3,4-dimethoxybenzyl)-4-(3,4-methylenedioxyphenyl)-3-pyrrolidinemethanol sulfate In view of various tests, including that mentioned above, the compounds of the invention and pharmaceutically acceptable acid addition salts thereof can be safely administered for the treatment of diseases of the heart and circulation such as various arrhythmia, angina pectoris, cardiac infarction, thrombosis and the like, in the form of a pharmaceutical preparation with a suitable and conventional pharmaceutically acceptable carrier, without adversely affecting the patients.

The pharmaceutical preparations can take any conventional form such as tablets, capsules, powders or injections.

Formulation Examples a. 10 mg tablets are prepared from the following compositions:

| | |
| --- | --- |
| Compound (I) or its salt | 10 mg |
| Lactose | 60 |
| Starch | 29 |
| Methyl Cellulose | 0.3 |
| Magnesium Stearate | 0.7 |
| | 100 mg | b. 10 mg injections are prepared from the following compositions:

| | |
| --- | --- |
| Compound (I) or its salt | 10 mg |
| Glucose | 100 mg |
| Water for Injection | A sufficient quantity to make 2 ml |

The daily dose of compound (I) or a salt thereof for human adults usually ranges from 30 to 60 mg for oral administration and from 5 to 10 mg for intravenous or intramuscular administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

8.8 g of ethyl 3-(3,4-dimethoxybenzyl)-4-(3,4-dimethoxyphenyl)-2-oxo-3-pyrrolidinecarboxylate is added to a mixture of a 70% solution of 20 g of sodium dihydrobis(2-methoxyethoxy)aluminate in benzene and 20 ml of anhydrous benzene at 0°–5°C with stirring. Upon completion of the addition, the mixture is held at 0°–5°C with stirring for one hour and then refluxed for an additional two hours. Sufficient acetone is then added to the reaction mixture under ice cooling to decompose excess hydride, and sufficient 25% aqueous potassium hydroxide solution to dissolve the precipitated alumina. The resulting solution is saturated with potassium carbonate. The organic layer is separated and extracted with 15% hydrochloric acid. The acid extract is made alkaline with an aqueous potassium hydroxide solution, and the separated oil is extracted with chloroform. The chloroform extract is washed with water, dried over anhydrous magnesium sulfate and concentrated under reduced pressure. The residual oil (crude product) is converted into the sulfate in ethanol with sulfuric acid, and the crude sulfate is recrystallized from aqueous ethanol to give 5.6 g of 3-(3,4-dimethoxybenzyl)-4-(3,4-dimethoxyphenyl)-3-pyrrolidinemethanol sulfate as white crystals, melting at 226°–229°C with decomposition.

The same product can also be produced by reducing 9.1 g of ethyl 3-(3,4-dimethoxybenzyl)-4-(3,4-dimethoxyphenyl)-2-thioxo-3-pyrrolidinecarboxylate with 20 g of sodium dihydrobis(2-methoxyethoxy)aluminate, in the same manner mentioned above.

EXAMPLE 2

8.5 g of ethyl 3-(3,4-dimethoxybenzyl)-4-(3,4-methylenedioxyphenyl)-2-oxo-3-pyrrolidinecarboxylate is added to a solution of 3.5 g of lithium aluminium hydride in 150 ml of anhydrous tetrahydrofuran with stirring, and the resulting mixture is refluxed for 8 hours. Then 30 ml of water is added to the reaction mixture under ice cooling, and the aqueous mixture is allowed to stand overnight. The insoluble matter is filtered off, the filtrate is evaporated to dryness. To the residue is added ethanol, and the insoluble matter is filtered off. Sulfuric acid is added to the filtrate, and precipitated solid is recrystallized from aqueous ethanol to give 4.9 g of 3-(3,4-dimethoxybenzyl)-4-(3,4-methylenedioxyphenyl)-3-pyrrolidinemethanol sulfate, melting at 231°–234°C with decomposition.

EXAMPLE 3

Ethyl 3-(3,4,5-trimethoxybenzyl)-4-(3,4-dimethoxyphenyl)-2-oxo-3-pyrrolidinecarboxylate (9.4 g), a 70% solution of sodium dihydrobis(2-methoxyethoxy)aluminate in benzene (20 g) and anhydrous benzene (20 ml) are treated in accordance with the procedure of Example 1 to give 6 g of 3-(3,4,5-trimethoxybenzyl)-4-(3,4-dimethoxyphenyl)-3-pyrrolidinemethanol sulfate, melting at 220°–223°C with decomposition.

EXAMPLE 4

4-Ethyl-3-(3,4-dimethoxybenzyl)-2-oxo-3-pyrrolidinecarboxylic acid (6.1 g), a 70% solution of sodium dihydrobis(2-methoxyethoxy)aluminate in benzene (35 g) and anhydrous benzene (35 ml) are treated in accordance with the procedure of Example 1 to give 2.6 g of 4-ethyl-3-(3,4-dimethoxybenzyl)3-pyrrolidinemethanol sulfate, melting at 182°–185°C.

Using the procedure set forth in the above examples, but substituting equivalent amount of the appropriate starting material, the following substituted pyrrolidinemethanols are also produced:

1. 4-(3,4-Dimethoxyphenyl)-3-(3,4-methylenedioxybenzyl)-3-pyrrolidinemethanol sulfate, M.p. 224°–230°C (decomposition)
2. 4-(4-Chlorophenyl)-3-(3,4-dimethoxybenzyl)-3-pyrrolidinemethanol sulfate, M.p. 250°–252°C (decomposition)
3. 3-(3,4-Dimethoxybenzyl)-4-(2-methoxyphenyl)-3-pyrrolidinemethanol sulfate, M.p. 160°–165°C
4. 3-(3,4-Dimethoxybenzyl)-4-(4-methoxyphenyl)-3-pyrrolidinemethanol sulfate, M.p. 249°–252°C (decomposition)
5. 3-(3,4-Dimethoxybenzyl)-4-phenyl-3-pyrrolidinemethanol, M.p. 152°–154°C; its sulfate, M.p. 244°–247°C (decomposition)
6. 3-(4-Chlorobenzyl)-4-ethyl-3-pyrrolidinemethanol hydrochloride, M.p. 160°–161°C
7. 3-(4-Chlorobenzyl)-4-(4-chlorophenyl)-3-pyrrolidinemethanol, M.p. 157°–158°C
8. 3-(3,4-Dimethoxybenzyl)-4-(3,4-dimethoxyphenyl)-1-methyl-3-pyrrolidinemethanol hydrochloride, M.p. 209°–210°C
9. 3-(2-Methoxybenzyl)-4-(3,4-dimethoxyphenyl)-3-pyrrolidinemethanol sulfate, M.p. 251°–255°C (decomposition)
10. 4-(3,4-Dimethoxyphenyl)-3-(4-methylbenzyl)-3-pyrrolidinemethanol sulfate, M.p. 238°–241°C (decomposition)
11. 3-(4-Chlorobenzyl)-4-(3,4-dimethoxyphenyl)-3-pyrrolidinemethanol sulfate, M.p. 239°–241°C (decomposition)
12. 3-Benzyl-4-(3,4-dimethoxyphenyl)-3-pyrrolidinemethanol sulfate, M.p. 243°–247°C (decomposition)
13. 3-Benzyl-4-phenyl-3-pyrrolidinemethanol hydrochloride, M.p. 206°–207°C
14. 3-(3,4-Dimethoxybenzyl)-4-(4-methylphenyl)-3-pyrrolidinemethanol sulfate, M.p. 260°–263°C (decomposition)
15. 3-(4-Methoxybenzyl)-4-(3,4-methylenedioxyphenyl)-3-pyrrolidinemethanol sulfate, M.p. 233°–235°C (decomposition)
16. 3-(3,4-Dimethoxybenzyl)-4-(3,4,5-trimethoxyphenyl)-3-pyrrolidinemethanol sulfate, M.p. 228°–230°C (decomposition)
17. 3-(4-Methoxy-α-methylbenzyl)-4-(3,4-dimethoxyphenyl)-3-pyrrolidinemethanol, its oxalate, M.p. 256°–259°C (decomposition); its sulfate, M.p. 254°–258°C (decomposition)
18. 4-(1-Ethylpentyl)-3-(3,4-dimethoxybenzyl)-3-pyrrolidinemethanol.

STARTING MATERIALS

The starting materials, namely compounds of formula (II) to be used in the production of the compounds of the present invention, can be prepared by reacting a compound of the formula:

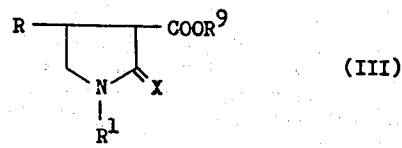

wherein R, $R^1$, $R^9$ and X are as defined above, with a compound of the formula:

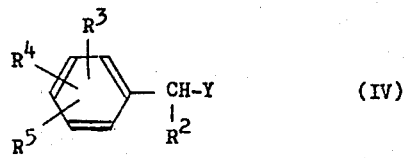

wherein $R^2$, $R^3$, $R^4$ and $R^5$ are as defined above, and Y is a halogen atom or a reactive group such as p-tolylsulfonyloxy.

The reaction is carried out in an inert solvent such as benzene, toluene, methanol, ethanol, dioxane, tetrahydrofuran or dimethylformamide, in the presence of an acid acceptor such as sodium, sodium alkoxide or sodium hydride, at a temperature of from room temperature to a refluxing temperature, for 0.5 to several hours.

The compounds of formula (II) wherein X is a sulfur atom can also be prepared by reacting a compound of formula (II) wherein X is an oxygen atom with diphosphorus pentasulfide, in an inert solvent such as benzene, toluene or pyridine, at a temperature of from room temperature to a refluxing temperature, for 0.5 to several hours.

The above compounds of formula (III) can be prepared, for example, by the method described in "J. Am. Chem. Soc.", vol. 66, pp. 1883–1884 (1944), "Chem. Abstr.", vol. 54, p. 12107g or "Bull. Soc. Chim. France", 1962, pp. 598–603.

Specific examples of the preparation of the starting materials of formula (II) are as follows.

Preparation 1

5.3 g of a 50% suspension of sodium hydride in mineral oil is added to a solution of 29.3 g of ethyl 4-(3,4-dimethoxyphenyl)-2-oxo-3-pyrrolidinecarboxylate in 180 ml of anhydrous dimethylformamide at 0°–5°C with stirring. The resulting mixture is held at 0°–5°C with stirring for 30 minutes and then at room temperature for an additional one hour. To the mixture is added 20.5 g of 3,4-dimethoxybenzyl chloride at 0°–5°C, and the whole mixture is stirred at room temperature for one hour. The reaction mixture is then concentrated under reduced pressure. Water is added to the residue, and the aqueous mixture is extracted with ethyl acetate. The extract is washed with water, dried over anhydrous magnesium sulfate and concentrated under reduced pressure. The residual oil is crystallized with ethanol to give 34.1 g of ethyl 3-(3,4-dimethoxybenzyl)-4-(3,4-dimethoxyphenyl)-2-oxo-3-pyrrolidinecarboxylate as white crystals, melting at 146°–149°C.

Preparation 2

A solution of 9.9 g of ethyl 4-(3,4-methylenedioxyphenyl)-2-oxo-3-pyrrolidinecarboxylate in 40 ml of absolute ethanol is added to a solution of 0.9 g of sodium in 50 ml of absolute ethanol at room temperature with stirring. The stirring is continued for one hour. To the mixture is added 8 g of 3,4-dimethoxybenzyl chloride. The resulting mixture is held at room temperature with stirring for one hour and then refluxed for an additional two hours. The ethanol is then removed under reduced pressure, water is added to the residue, and the aqueous mixture is extracted with ethyl acetate. The extract is washed with water, dried over sodium sulfate and concentrated under reduced pressure. The residue is recrystallized from ethanol to give 11.5 g of ethyl 3-(3,4-dimethoxybenzyl)-4-(3,4-methylenedioxyphenyl)-2-oxo-3-pyrrolidinecarboxylate, melting at 167°–168°C.

Preparation 3

A mixture of 6 g of ethyl 3-(3,4-dimethoxybenzyl)-4-(3,4-dimethoxyphenyl)-2-oxo-3-pyrrolidinecarboxylate, 4 g of diphosphorus pentasulfide and 120 ml of anhydrous benzene is refluxed with stirring for one hour. While it is hot, the insoluble matter is filtered off, and the filtrate is concentrated under reduced pressure. The residue is washed with water and recrystallized from ethanol to give 5.4 g of ethyl 3-(3,4-dimethoxybenzyl)-4-(3,4-dimethoxyphenyl)-2-thioxo-3-pyrrolidinecarboxylate as white crystalline powder, melting at 166°–169°C.

Although the present invention has been adequately discussed in the foregoing specification and examples included therein, one readily recognizes that various changes and modifications may be made without departing from the spirit and scope thereof.

What is claimed is:

1. A substituted pyrrolidinemethanol of the formula:

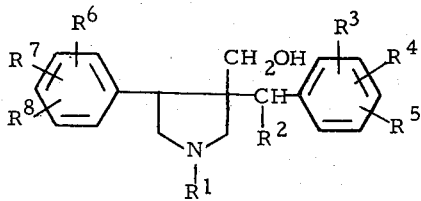

wherein $R^1$ and $R^2$ are each a hydrogen atom or an alkyl group of 1 to 4 carbon atoms; $R^3$, $R^4$, $R^5$, $R^6$, $R^7$ and $R^8$ are each a hydrogen atom, a halogen atom, an alkyl group of 1 to 4 carbon atoms or an alkoxy group of 1 to 4 carbon atoms, or $R^3$ and $R^4$, or $R^6$ and $R^7$ combinedly form a methylenedioxy group; and pharmaceutically acceptable acid addition salts thereof.

2. A substituted pyrrolidinemethanol of the formula:

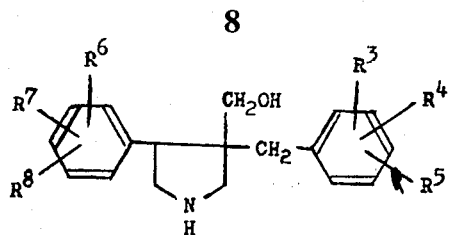

wherein each symbol is as recited in claim 1; and pharmaceutically acceptable acid addition salts thereof.

3. The compound of claim 1:
3-(3,4-Dimethoxybenzyl-4-(3,4-dimethoxyphenyl)-3-pyrrolidinemethanol.

4. The compound of claim 1:
3-(3,4-Dimethoxybenzyl)-4-(3,4-methylenedioxyphenyl)-3-pyrrolidinemethanol.

5. The compound of claim 1:
3-(3,4,5-Trimethoxybenzyl)-4-(3,4-dimethoxyphenyl)-3-pyrrolidinemethanol.

6. The compound of claim 1:
4-(3,4-Dimethoxyphenyl)-3-(3,4-methylenedioxybenzyl)-3-pyrrolidinemethanol.

7. The compound of claim 1:
4-(4-Chlorophenyl)-3-(3,4-dimethoxybenzyl)-3-pyrrolidinemethanol.

8. The compound of claim 1:
3-(3,4-Dimethoxybenzyl)-4-(2-methoxyphenyl)-3-pyrrolidinemethanol.

9. The compound of claim 1:
3-(3,4-Dimethoxybenzyl)-4-(4-methoxyphenyl)-3-pyrrolidinemethanol.

10. The compound of claim 1:
3-(3,4-Dimethoxybenzyl)-4-phenyl-3-pyrrolidinemethanol.

11. The compound of claim 1:
3-(4-Chlorobenzyl)-4-(4-chlorophenyl)-3-pyrrolidinemethanol.

12. The compound of claim 1:
3-(3,4-Dimethoxybenzyl)-4-(3,4-dimethoxyphenyl)-1-methyl-3-pyrrolidinemethanol.

13. The compound of claim 1:
3-(2-Methoxybenzyl)-4-(3,4-dimethoxyphenyl)-3-pyrrolidinemethanol.

14. The compound of claim 1:
4-(3,4-Dimethoxyphenyl)-3-(4-methylbenzyl)-3-pyrrolidinemethanol.

15. The compound of claim 1:
3-(4-Chlorobenzyl)-4-(3,4-dimethoxyphenyl)-3-pyrrolidinemethanol.

16. The compound of claim 1:
3-Benzyl-4-(3,4-dimethoxyphenyl)-3-pyrrolidinemethanol.

17. The compound of claim 1:
3-Benzyl-4-phenyl-3-pyrrolidinemethanol.

18. The compound of claim 1:
3-(3,4-Dimethoxybenzyl)-4-(4-methylphenyl)-3-pyrrolidinemethanol.

19. The compound of claim 1:
3-(4-Methoxybenzyl)-4-(3,4-methylenedioxyphenyl)-3-pyrrolidinemethanol.

20. The compound of claim 1:
3-(3,4-Dimethoxybenzyl)-4-(3,4,5-trimethoxyphenyl)-3-pyrrolidinemethanol.

21. The compound of claim 1:
3-(4-Methoxy-α-methylbenzyl)-4-(3,4-dimethoxyphenyl)-3-pyrrolidinemethanol.

* * * * *